(12) United States Patent
Oshika et al.

(10) Patent No.: US 6,776,803 B2
(45) Date of Patent: Aug. 17, 2004

(54) HAIR DYE COMPOSITIONS

(75) Inventors: Masato Oshika, Tokyo (JP); Takashi Itou, Tokyo (JP); Eiichi Nishizawa, Tokyo (JP); Sachiko Tajima, Tokyo (JP); Takashi Mizooku, Tokyo (JP)

(73) Assignee: Kao Corporation, Tokyo (JP)

( * ) Notice: Subject to any disclaimer, the term of this patent is extended or adjusted under 35 U.S.C. 154(b) by 107 days.

(21) Appl. No.: 10/060,200

(22) Filed: Feb. 1, 2002

(65) Prior Publication Data

US 2003/0066141 A1 Apr. 10, 2003

(30) Foreign Application Priority Data

| Feb. 15, 2001 | (JP) | .................................. | 2001-038780 |
| Feb. 15, 2001 | (JP) | .................................. | 2001-038781 |
| Feb. 15, 2001 | (JP) | .................................. | 2001-038782 |
| Feb. 15, 2001 | (JP) | .................................. | 2001-038783 |

(51) Int. Cl.$^7$ ................................................. A61K 7/13
(52) U.S. Cl. ........................ 8/405; 8/455; 8/576; 8/578; 8/607
(58) Field of Search ...................... 8/405, 455, 463, 8/576, 578, 579, 594, 607, 611

(56) References Cited

U.S. PATENT DOCUMENTS

| 5,332,581 A | * | 7/1994 | Yoshihara et al. ............. 424/70 |
| 5,500,154 A | | 3/1996 | Bacon et al. ................ 252/551 |
| 6,204,229 B1 | | 3/2001 | Hasegawa et al. .......... 510/101 |

FOREIGN PATENT DOCUMENTS

| DE | 102 00 185 | | 7/2002 | |
| EP | 0 161 073 | | 11/1985 | |
| EP | 1 022 014 | | 7/2000 | |
| EP | 1 022 014 A1 | * | 7/2000 | ............ A61K/7/13 |
| GB | 2259717 | | 3/1993 | |
| JP | 48-23911 | | 7/1973 | |
| JP | 51-151341 | | 12/1976 | |
| JP | Sho 51-151-341 | | 12/1976 | |
| JP | 61-210023 | | 9/1986 | |
| JP | 5-78228 | | 3/1993 | |
| JP | 5-230496 | | 9/1993 | |
| JP | 5-238923 | | 9/1993 | |
| JP | 5-310543 | | 11/1993 | |
| JP | 7-101841 | | 4/1995 | |
| JP | 7-103964 | | 4/1995 | |
| JP | 8-245348 | | 9/1996 | |
| JP | 9-255540 | | 9/1997 | |
| JP | 10-53970 | | 2/1998 | |
| JP | 10-87450 | | 4/1998 | |
| JP | 10-507789 | | 7/1998 | |
| JP | 231234 | | 9/1998 | |
| JP | 10231234 | * | 9/1998 | ............ A61K/7/13 |
| JP | 10-245327 | | 9/1998 | |
| JP | 10-259121 | | 9/1998 | |
| JP | 10-259122 | | 9/1998 | |
| JP | 10-259123 | | 9/1998 | |
| JP | Hei 11-349453 | | 12/1999 | |
| JP | 11-349453 | | 12/1999 | |
| JP | 2000-16929 | | 1/2000 | |
| JP | 2000-186018 | | 7/2000 | |
| JP | 2000-290680 | | 10/2000 | |

* cited by examiner

*Primary Examiner*—Brian P. Mruk
*Assistant Examiner*—Eisa Elhilo
(74) *Attorney, Agent, or Firm*—Oblon, Spivak, McClelland, Maier & Neustadt, P.C.

(57) ABSTRACT

A hair dye composition comprises the following ingredients (A) and (B):

(A) a compound having a 5- or 6-membered lactone skeleton, and (B) an acid dye; and having a pH of from 2 to 6 and a buffer capacity not lower than 0.004 gram equivalent/L but lower than 0.2 gram equivalent/L as measured in a form of a tenfold dilute aqueous solution. This hair dye composition does not cause staining to the skin, is excellent in dyeing properties for hair, is good in the fastness to shampoo, and does not give off gas through hydrolysis in an acidic range.

16 Claims, No Drawings

HAIR DYE COMPOSITIONS

TECHNICAL FIELD

This invention relates to hair dye compositions having excellent dyeing properties for hair and good fastness to shampoo without causing staining to the scalp or skin.

BACKGROUND ART

Acidic hair dye compositions with various organic solvents, typified by benzyl alcohol, contained as penetrant solvents (JP 61-210023 A, JP 7-101841 A, etc.) involve a problem in that upon dyeing, they tend to stain the scalp and skin at the same time, although their penetration into hair is good.

It has, therefore, been a conventional practice to thicken these compositions with a water-soluble high-molecular substance or the like such that they are prevented from dripping or running o f to reduce staining to the skin. This conventional practice is, however, still unable to bring about any substantial solution to the problem (JP 10-87450 A, JP 9-255540 A, JP 8-245348 A, etc.). It has also been proposed to lower the skin staining tendency with an aromatic alcoholic compound, a lower alkylene carbonate or the like (JP 10-53970 A, JP 48-23911 B). This approach, however, cannot bring about sufficient effects either.

With the foregoing circumstances in view, the present assignee developed an acidic hair dye composition having excellent dyeing properties for hair and good shampoo fastness with a reduced tendency of staining to the skin by adding a lower alkylene carbonate as a penetrant solvent and also adjusting the buffer capacity of the composition to a specific range (JP 2000-186018 A).

As the lower alkylene carbonate undergoes hydrolysis in an acidic range and gives off carbon dioxide, packaging of the acidic hair dye composition in a container of the closed system leads to problems such as bulging of the container and leakage of liquid upon application. It is hence required to provide the container with a special means such as a vent.

DISCLOSURE OF THE INVENTION

An object of the present invention is, therefore, to provide a hair dye composition, which has low staining tendency to the skin and excellent dyeing properties for hair and does not give off gas through hydrolysis even in an acidic range.

The present inventors have now found that an acidic hair dye composition, which has low staining tendency to the skin, excellent dyeing properties for hair and good shampoo fastness and does not give off gas through hydrolysis even in an acidic range, can be obtained when a 5-membered or 6-membered cyclic lactone compound is added as a penetrant solvent and the buffer capacity of the composition is adjusted to a particular range.

The present invention, therefore, provides a hair dye composition comprising the following ingredients (A) and (B):

(A) a compound having a 5- or 6-membered lactone skeleton, and
(B) an acid dye; and having a pH of from 2 to 6 and a buffer capacity not lower than 0.004 gram equivalent/L but lower than 0.2 gram equivalent/L as measured in a form of a tenfold dilute aqueous solution.

The present invention also provides a method of dyeing hair, which comprises applying the above-described hair dye composition onto the hair.

BEST MODES FOR CARRYING OUT THE INVENTION

As the lactone compound for use as the ingredient (A) in the present invention, one represented by the following formula (1) or (2) is preferred:

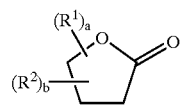

(1)

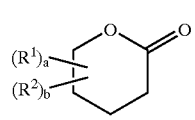

(2)

wherein $R^1$ and $R^2$ represent different substituent groups, respectively, and a and b each stands for 0 or 1.

Preferred examples of $R^1$ and $R^2$ in the formulas (1) and (2) can include linear, branched or cyclic alkyl groups, hydroxyl group, sulfonic group, phosphoric group, carboxyl group, phenyl group, sulfoalkyl groups, alkylphosphate groups, and carboxyalkyl groups. Of these, preferred are linear or branched alkyl groups having 1 to 6 carbon atoms, for example, methyl group, ethyl group, propyl group, isopropyl group, butyl group and the like, substituted to the γ-position in the case of γ-lactone or to the δ-position (in other words, a methylene group adjacent to the hetero-oxygen atom) in the case of δ-lactone. If it is desired to impart higher water-solubility to the lactone compounds (1) and (2), inclusion of an acidic group such as sulfonic group, phosphoric group or carboxylic group or an alkyl group substituted by such an acidic group as $R^1$ or $R^2$ is preferred. Specific examples of the lactone compounds (1) and (2) can include γ-butyrolactone, γ-pentanolactone, γ-hexanolactone, γ-heptanolactone, δ-pentanolactone, δ-hexanolactone, and δ-heptanolactone. Among these, γ-lactones, especially γ-hexanolactone and γ-heptanolactone are preferred for their stability and the resulting hair dyeing properties.

As the ingredient (A), two or more lactone compounds may be used in combination. From the standpoint of exhibiting sufficient hair dyeing properties and also preventing the staining to the skin, the content of the ingredient (A) may range preferably from 0.5 to 50 wt. %, more preferably from 5 to 50 wt. %, notably from 10 to 35 wt. %.

No particular limitation is imposed on the acid dye for use as the ingredient (B) in the present invention insofar as it is a water-soluble acid dye. Illustrative are Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Red 92 (C.I. 45410), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C. I.

20470), Acid Black 52 (C. I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C. I. 15685), and Brilliant Black 1 (C.I. 28440).

As the ingredient (B), two or more of such acid dyes may be used in combination. It is preferred to include Acid Black 1 or Acid Orange 7, especially Acid Orange 7. From the standpoint of exhibiting sufficient dyeing effects and also reducing the staining to the hands and skin, the content of the ingredient (B) may range preferably from 0.05 to 5 wt. %, more preferably from 0.1 to 4 wt. %, notably from 0.2 to 3 wt. % based on the whole composition.

From the standpoint of preventing damage to hair and roughening of the scalp, hands and skin by the acidic ingredient and exhibiting penetration promoting effect for the acid dye, the hair dye composition according to the present invention is required to have a pH of from 2 to 6, with a pH range of from 2 to 5 being preferred and a pH range of from 2.5 to 4 being more preferred.

From the standpoint of exhibiting sufficient hair dyeing effects and also reducing the skin staining tendency, the hair dye composition according to the present invention is required to have a buffer capacity not lower than 0.004 gram equivalent/L but lower than 0.2 gram equivalent/L, preferably not lower than 0.01 gram equivalent/L but lower than 0.2 gram equivalent/L, more preferably not lower than 0.015 gram equivalent/L but lower than 0.2 gram equivalent/L as measured in a form of a tenfold dilute aqueous solution. The term "buffer capacity" as used herein means a value determined by the following formula while using as a scale the concentration of a base required to raise the pH of the aqueous solution at 25° C. by 1 from an initial value.

$$\text{Buffer capacity} = |dC_B/dpH|$$

wherein $C_B$ represents an ion concentration(gram equivalent/L) of the base.

Such a buffer capacity can be imparted by adding a pH buffering agent or the like to the hair dye composition. Usable as the pH buffering agent is an organic acid or inorganic acid or a salt thereof, which has buffering action in the pH range of from 2.0 to 6.0. Examples of the organic acid can include citric acid, glucolic acid, succinic acid, tartaric acid, lactic acid, fumaric acid, malic acid, levulinic acid, butyric acid, valeric acid, oxalic acid, maleic acid, and mandelic acid. Examples of the inorganic acid can include phosphoric acid, sulfuric acid, and nitric acid. Further, examples of the salt of such an acid can include its alkali metal salts such as the sodium salt and the potassium salt; its ammonium salt; and its alkanolamine salts such as the triethanolamine salt. No particular limitation is imposed on the amount of the pH buffering agent to be added, and its amount varies depending on the kind of the compound giving buffering ability. When sodium citrate is used as a primary compound giving the buffering ability, for example, it can be added at a concentration of about 1 wt. % or higher.

In the hair dye composition according to the present invention, the addition of the ingredient (A) has made it possible to increase the rate and quantity of penetration of the acid dye into hair to levels at least comparable with those available from benzyl alcohol or the like which has been commonly employed as a penetration promoter to date. If a hair dye composition making use of benzyl alcohol or the like is brought into contact with the skin, the skin is stained so strongly that it cannot be easily removed by usual washing. With the hair dye composition according to the present invention in which the ingredient (A) is used as a penetration promoter and the buffer capacity has been adjusted to the above-described range, no substantial staining takes place even when the hair dye composition is kept in contact with normal skin for a long time although it exhibit high hair dyeing properties. Even if the staining of skin should occur due to a reduction in the skin barrier function for skin roughening or the like or due to an individual difference, the stain can be easily removed, for example, by washing it with shampoo or the like. Unlike the use of a lower alkylene carbonate as a penetration promoter, the hair dye composition according to the present invention is free of the troublesome production of gas through hydrolysis in an acidic range.

The hair dye composition according to the present invention can additionally contain, as an ingredient (C), a fragrance composition, which comprises a combination of a fragrance substance having a ClogP value not greater than 1.5 and another fragrance substance having a ClogP value not smaller than 3.0. Because the lactone compound as the ingredient (A) is a penetration promoter, the lactone compound by itself penetrates into hair. A slightly sweet, greenish smell associated with the lactone and its hydrolysates, therefore, remains on the hair for a long time, so that combined use of a general formulated fragrance gives off a poorly-balanced smell, leading to a problem that this smell makes the user very uncomfortable. However, the use of the fragrance composition, which comprises the fragrance substances having the above-specified ClogP values, respectively, has made it possible to obtain a smell well harmonized with the slightly sweet, grassy smell derived from the lactone-base penetration promoter.

The fragrance composition used as the ingredient (C) in the present invention is the combination of the fragrance substance having a ClogP value not greater than 1.5, preferably of from 1.0 to 1.5 and the fragrance substance having a ClogP value not smaller than 3.0, preferably of from 3.0 to 5.0. The term "ClogP value" as used herein means a common logarithmic value of a 1-octanol/water partition coefficient P, which represents a ratio of an equilibrium concentration of a compound in 1-octanol to an equilibrium concentration of the compound in water. This ClogP value is determined by a fragment approach based on the chemical structure of the compound (A. Leo, Comprehensive Medical Chemistry, Vol.4; C. Hansch, P. G. Sammens, J. B. Taylor and C. A. Ramden, Eds., P 295, Pergramon Press, 1990), and is defined by a value calculated by the "CLOGP" program available from Daylight Chemical Information Systems, Inc.

Examples of the fragrance substance the ClogP value of which is not greater than 1.5 can include vanillin (1.354), cinnamic alcohol (1.400), heliotropine (1.257), coumarin (1.412), 2-methyl-3-(3,4-methylenedioxyphenyl)-propanal (helional; 1.387), 4-(4-hydroxyphenyl)-2-butanone (raspberry ketone; 1.072), benzaldehyde (1.495), anisic alcohol (1.023), cis-3-hexenol (1.397), 3,4-dimethoxybenzaldehyde (methylvanillin; 1.350), heliotropyl acetate (1.315), phenylacetaldehyde dimethylacetal (1.293), phenylacetaldehyde glyceryl acetal (0.833), phenylacetic acid (1.414), phenylethyl alcohol (1.183), phenoxyethyl alcohol (1.188), sugar lactone (0.888), furaneol (0.413), maltol (−0.062), and ethylmaltol (0.467) (the parenthesized values indicate the corresponding ClogP values). Of these, preferred are vanillin, cinnamic alcohol, heliotropine, coumarin, 2-methyl-3-(3,4-methylenedioxyphenyl)-propanal, 4- (4-hydroxyphenyl)-2-butanone, benzaldehyde, anisic alcohol, cis-3-hexenol, phenylaldehyde dimethyl acetal, phenylethyl alcohol, and phenoxyethyl alcohol. Two or more of these fragrance substances may be used in combination.

The fragrance substance the ClogP value of which is not smaller than 3.0 is a hydrophobic fragrance substance generally known as a fragrance substance having high fragrance retention. Specific examples can include 2,6-dimethyl-octen-2-ol (3.033), methyl octin carbonate (3.097), methyl chavicol (estragole; 3.134), 3-methyl-5-phenyl-1-pentanol (3.169), β-naphthyl methyl ether (3.235), 2-butyl-4,4,6-trimethyl-1,3-dioxane (3.244), 3,7-dimethyl-6-octen-1-ol (3.253), anethole (3.314), ethyl tricyclo[5.2.1.0$^{2,6}$]decan-2-ylcarboxylate (3.370), 2-methyl-5-isopropylphenol (3.401), 3,7-dimethyl-1,6-octadien-3-yl acetate (3.495), 3,7-dimethyloctan-3-ol (3.517), isobornyl acetate (3.525), p-menthen-8-yl acetate (3.575), 1-(4-isopropylcyclohexyl)ethanol (3.642), 5-(2,6,6-trimethyl-2-cyclohexen-1-yl)-4-pentan-3-one (3.710), 3,7-dimethyl-2,6-octadien-1-yl acetate (3.715), 4-cyclohexyl-4-methyl-2-pentanone (3.769), 4-(2,2,6-trimethyl-1-cyclohexen-1-yl)-3-buten-2-one (3.770), 2,5,5-trimethyl-1,2,3,4,4α,5,6,7-octahydro-2-naphthalenol (3.772), 2,6-dinitro-3,5-dimethyl-4-t-butylbenzene (3.782), δ-undecalactone (3.860), 2-methyl-4-(2,2,3-trimethyl-3-cyclopenten-1-yl)-2-buten-1-ol (3.902), α-santalol (3.906), allyl 3-cyclohexylpropionate (3.935), 1-(2-t-butyl-cyclohexyloxy)-2-butanol (3.969), 2-heptylcyclopentanone (3.999), 5-(2,6,6-trimethyl-2-cyclohexen-1-yl)-3-methyl-3-buten-2-one (4.019), phenylethyl benzoate (4.058), diphenylmethane (4.059), o-t-butylcyclohexyl acetate (4.059), p-t-butylcyclohexyl acetate (4.059), p-methyl-isopropylbenzene (4.068), 4-(2,2,5,6-tetramethyl-2-cyclohexen-1-yl)-3-buten-2-one (4.229), diphenyl oxide (4.240), p-mentha-1,8-diene (4.352), 2,2,5-trimethyl-5-pentylcyclopentanone (4.498), cedrol (4.530), patchouli alcohol (4.530), 7-acetyl-1,2,3,4,5,6,7,8-octahydro-1,1,6,7-tetramethylnapht halene (4.650), pisabolol (4.660), 1-(2,6,6-trimethyl-1-cyclohexen-1-yl)-2-buten-1-one (4.710), 3,7,11-trimethyl-2,6,10-dodecatrien-12-ol (4.800), vetiveryl acetate (5.092), cedryl methyl ether (5.106), 3α,6,6,9α-tetramethyldodecahydronaphtho[2,1-b]furan (5.266), 6-acetyl-1,1,2,3,3,5-hexamethylindane (5.688), 1-(2,2,6-trimethylcyclohexyl)-3-hexanol (5.868), 4,6,6,7,8,8-hexamethyl-1,3,4,6,7,8-hexahydrocyclopentabenzo pyran (6.062), α-cedrene (6.133), 7-cyclohexadecenolide (6.361), 3-methylcyclopentadecanone (6.415), 9-cyclopentadecen-1-one (6.530), hexadecanolide (6.845), labdenol (7.228), 3,7,11,15-tetramethyl-2-hexadecen-1-ol (8.283), 3.7-dimethyl-2,6-octadienal (citral; 3.12), p-menthan-3-ol (L-menthol; 3.233), 3,7-dimethyl-6-octen-1-ol (citronellal; 3.264), 1-(2,6,6-trimethyl-2-cyclohexen-1-yl)-2-buten-1-one (α-damascone; 3.62), p-tert-butyl-α-methylhydrocinnamic aldehyde (lilial; 3.858), 6-acetyl-1,1,2,4,4,7-hexamethyltetralin (tentalome; 6.247), and cyclopentadecanolide (pentalide; 6.286) (the parenthesized values indicate the corresponding ClogP values). Among these, preferred are 2,6-dimethyl-7-octene-2-ol, 3-methyl-5-phenyl-1-pentanol, 3,7-dimethyl-6-octen-1-ol, ethyl tricyclo [5.2.1.0$^{2,6}$]decan-2-ylcarboxylate, 2,6-dinitro-3,5-dimethyl-4-t-butylbenzene, 2-methyl-4-(2,2,3-trimethyl-3-cyclopenten-1-yl)-2-buten-1-ol, 1-(2-t-butylcyclohexyloxy)-2-butanol, 5-(2,6,6-trimethyl-2-cyclohexen-1-yl)-3-methyl-3-buten-2-one, p-mentha-1,8-diene, 7-acetyl-1,2,3,4,5,6,7,8-octahydro-1,1,6,7-tetramethylnapht halene, 3,7-dimethyl-2,6-octadienal, methyl chavicol, p-menthan-3-ol, 3,7-dimethyl-6-octen-1-ol, 1-(2,6,6-trimethyl-2-cyclohexen-1-yl)-2-buten-1-one, and p-tert-butyl-α-methylhydrocinnamic aldehyde. Two or more of these fragrance substances may be used in combination.

From the standpoint of assuring a good balance with a smell associated with the ingredient (A) or its hydrolysates, the content of the ingredient (C)—in terms of the total content of the fragrance substance the ClogP value of which is not greater than 1.5 and the fragrance substance the ClogP value of which is not smaller than 3.0 —may preferably be in a range of from 0.05 to 1 wt. %, with a range of from 0.1 to 0.7 wt. % being particularly preferred, both based on the whole composition. Concerning the ratio of the two groups of fragrance substances used, it is preferred to use the fragrance substance, the ClogP value of which is not greater than 1.5, and the fragrance substance, the ClogP value of which is not smaller than 3.0, at a weight ratio of from 10:90 to 90:10.

To improve the dyeing properties further, it is preferred for the hair dye composition according to the present invention to additionally incorporate, as an ingredient (D), one or more organic solvents selected from benzyloxyethanol, benzyl alcohol, phenoxyethanol, phenoxyisopropanol, benzyl glycerol, N-benzylformamide, cinnamyl alcohol, phenethyl alcohol, p-anisyl alcohol, ethanol, 1-propanol, 2-propanol, 1-butanol, butoxyethanol, p-methylbenzyl alcohol, methyl carbitol, ethyl carbitol, and propyl carbitol. Of these, preferred are aromatic alcohol analogs, with benzyloxyethanol and benzyl alcohol being particularly preferred. From the standpoint of effectively improving the dyeing properties for hair and effectively preventing the staining to skin, the content of the ingredient (D) may range preferably from 0 to 10 wt. %, more preferably from 0.01 to 10 wt. %, notably from 0.1 to 5 wt. % based on the whole composition.

With a view to preventing dripping and smeary sticking onto the scalp upon use, the hair dye composition according to the present invention may additionally contain a water-soluble high-molecular substance as an ingredient (E). Illustrative of the water-soluble high-molecular substance are gum arabic, carrageenan, karaya gum, tragacanth gum, carob gum, quince seeds (marmelo), casein, dextrin, gelatin, sodium pectate, sodium alginate, methylcellulose, ethylcellulose, carboxymethyl-cellulose (CMC), hydroxyethylcellulose, hydroxypropyl-cellulose, polyvinyl alcohol (PVA), poly(vinyl methyl ether) (PVM), polyvinyl pyrrolidone (PVP), sodium polyacrylate, locust bean gum, guar gum, tamarind gum, dialkyldimethylammonium cellulose sulfates, xanthan gum, modified xanthan gum, wellan gum, lavor gum, gellan gum, carboxyvinyl polymer, acrylate ester/methacrylate ester copolymers, a partial crosslinking product of methyl vinyl ether/maleic anhydride copolymer by 1,9-decadiene, polyethylene glycol, magnesium aluminum silicate, and bentonite. Two or more of these water-soluble high-molecular substances may be used in combination. The content of the ingredient (E) may range preferably from 0.1 to 10 wt. %, notably from 0.5 to 5 wt. %.

With a view to enhancing the solubility of the ingredient (A) and ingredient (E), it is also possible to additionally incorporate a lower alcohol or polyol in the hair dye composition according to the present invention. Specific examples can include those having 2 to 4 carbon atoms, for example, ethanol, 2-propanol, 1-propanol, 1-butanol, ethylene glycol, propylene glycol, isopropylene glycol, 1,3-butylene glycol, and glycerin. Two or more of these lower alcohols and/or polyols may be used in combination. The content of the lower alcohol or polyol may range preferably from 0.1 to 30 wt. %, notably from 0.1 to 20 wt. % based on the whole composition.

In addition to the above-described ingredients, other ingredients that are usable in general cosmetics and the like may also be added to the hair dye composition according to the present invention as needed depending upon its application purpose. Illustrative of such other ingredients are surfactants, cationic polymers, alkalizing agents (ammonia, alkanolamines, etc.), hair conditioning agents, oil ingredients, silicone derivatives, other fragrances, preservatives, ultraviolet absorbers, chelating agents, stabilizers, antioxidants, disinfectants, and propellants. The hair dye composition according to the present invention can be produced in a manner commonly known in the art.

The hair dye composition according to the present invention can be used in exactly the same way as the conventional hair dye compositions. For example, the hair dye composition is dispensed onto a comb or brush as much as needed, and is then applied to the hair on the head. The hair dye composition is permitted to remain in contact with the hair for 1 to 30 minutes or so after the application. The thus-dyed hair is then shampooed and rinsed with water and dried.

In the following Examples, the "buffer capacity" of each composition was determined as will be described next. A 10-gram aliquot of the composition was measured, to which water was added to give a total volume of 100 mL. The pH of the resulting solution was measured. A 1 N aqueous solution of sodium hydroxide was next added to the solution to measure an amount (X mL) of the 1 N aqueous solution of sodium hydroxide which was required to raise the pH by 1. A value calculated in accordance with the following formula was recorded as the buffer capacity.

Buffer capacity=10×/1000 gram equivalent/L

EXAMPLE 1

An acidic hair dye composition of the formulation shown in Table 1 was prepared, and various tests were conducted.

(1) Ranking Method of Dyeing Properties for Goat's Wool and Shampoo Fastness

After the hair dye composition (1 g) was evenly applied to a tress of white goat's wool (1 g), the hair dye composition was permitted to remain in contact with the goat's wool for 15 minutes at 30° C. The thus-dyed tress was then washed with water, shampooed twice, rinsed once, and dried. By a panel of 20 experts, the tress was examined to determine the dyeing properties for the goat's wool. The examination results were ranked in accordance with the below-described ranking standards.

The tress was subjected to further shampooing and rinsing treatment 20 times in total, and dried. By the panel of 20 experts, the tress was examined to determine the shampoo fastness. The examination results were also ranked in accordance with the below-described ranking standards. The results are presented in Table 1.

Ranking Standards

A: At least 80% of the experts found the dyeing properties for goat's wool or the shampoo fastness to be good.

B: At least 50% but less than 80% of the experts found the dyeing properties for goat's wool or the shampoo fastness to be good.

C: At least 20% but less than 50% of the experts found the dyeing properties for goat's wool or the shampoo fastness to be good.

D: Less than 20% of the experts found the dyeing properties for goat's wool or the shampoo fastness to be good.

(2) Ranking Method of Skin Staining Avoidability and Wash-off Readiness

After the hair dye composition was evenly applied to the human forearm at a rate of 1 g per 10 cm$^2$, the hair dye composition was permitted to remain in contact with the forearm for 15 minutes at 30° C. The forearm was then washed with water to thoroughly remove the adhered hair dye composition from the skin of the forearm, and thereafter, the skin of the forearm was dried. By a panel of 20 experts, the forearm was examined to determine the avoidability of skin staining. The examination results were ranked in accordance with the below-described ranking standards.

The forearm was then cleaned with soap by massaging it 50 strokes, and dried. By the panel of 20 experts, the forearm was examined to determine the wash-off readiness. The examination results were also ranked in accordance with the below-described ranking standards. The results are presented in Table 1.

Ranking Standards

A: At least 80% of the experts found skin staining to be absolutely unnoticeable.

B: At least 50% but less than 80% of the experts found skin staining to be absolutely unnoticeable.

C: At least 20% but less than 50% of the experts found skin staining to be absolutely unnoticeable.

D: Less than 20% of the experts found skin staining to be absolutely unnoticeable.

(3) Determination Method of Production of Gas by Storage Over Time

The hair dye composition (90 g) was sealed in a 100-mL polypropylene container, and then stored at 50° C. for 30 days. After the container was left over at room temperature, the container was examined for a possible bulge to determine whether gas had been produced inside the container. The examination results are presented in Table 1.

TABLE 1

|  | Invention product, wt. % | | | | | Comparative product, wt. % | | | |
| --- | --- | --- | --- | --- | --- | --- | --- | --- | --- |
|  | 1 | 2 | 3 | 4 | 5 | 1 | 2 | 3 | 4 |
| Acid Black 1 | 0.1 | 0.1 | 0.1 | 0.1 | 0.1 | 0.1 | 0.1 | 0.1 | 0.1 |
| Acid Violet 43 | 0.05 | 0.05 | 0.05 | 0.05 | 0.05 | 0.05 | 0.05 | 0.05 | 0.05 |
| Acid Orange 7 | 0.1 | 0.1 | 0.1 | 0.1 | 0.1 | 0.1 | 0.1 | 0.1 | 0.1 |
| Benzyloxyethanol |  |  |  |  | 3 |  | 5 |  |  |

TABLE 1-continued

|  | Invention product, wt. % | | | | | Comparative product, wt. % | | | |
| --- | --- | --- | --- | --- | --- | --- | --- | --- | --- |
|  | 1 | 2 | 3 | 4 | 5 | 1 | 2 | 3 | 4 |
| Benzyl alcohol |  |  |  |  |  |  | 5 |  |  |
| Ethylene carbonate |  |  |  |  |  |  |  | 15 |  |
| Propylene carbonate |  |  |  |  |  |  |  |  | 15 |
| γ-Butyrolactone | 30 |  |  |  |  |  |  |  |  |
| γ-Hexanolactone |  | 10 |  |  | 5 |  |  |  |  |
| γ-Heptanolactone |  |  | 5 |  |  |  |  |  |  |
| γ-Pentanolactone |  |  |  | 4 |  |  |  |  |  |
| Ethanol | 5 | 5 | 5 | 5 | 5 | 5 | 5 | 5 | 5 |
| Citric acid | 4 | 4 | 4 | 4 | 4 | 4 | 4 | 4 | 4 |
| Caustic soda |  |  |  |  | q.s. to pH 3.0 |  |  |  |  |
| Hydroxyethylcellulose | 1.5 | 1.5 | 1.5 | 1.5 | 1.5 | 1.5 | 1.5 | 1.5 | 1.5 |
| Fragrance | 0.1 | 0.1 | 0.1 | 0.1 | 0.1 | 0.1 | 0.1 | 0.1 | 0.1 |
| Purified water |  |  |  |  | Balance |  |  |  |  |
| Buffer capacity (gram eq./L) | 0.02 | 0.02 | 0.02 | 0.02 | 0.02 | 0.02 | 0.02 | 0.02 | 0.02 |
| Dyeing properties for goat's wool | A | A | A | B | A | B | B | B | B |
| Shampoo fastness | B | B | B | B | A | B | B | B | B |
| Avoidability of skin staining | A | A | A | A | A | D | D | B | B |
| Wash-off readiness from skin | A | A | B | A | B | D | D | B | B |
| Production of gas by storage over time | None | None | None | None | None | None | None | Gas* | Gas* |

*Gas: Production of gas occurred.

EXAMPLE 2

Acidic hair dye compositions of the formulations shown in Table 2, respectively, were prepared. In a similar manner as in Example 1(1), their dying properties for goat's wool and shampoo fastness were ranked. The results are presented in Table 2.

TABLE 2

|  | Invention product, wt. % | | | Comparative product, wt. % |
| --- | --- | --- | --- | --- |
|  | 6 | 7 | 8 | 5 |
| Acid Black 1 | 0.1 | 0.1 | 0.1 | 0.1 |
| Acid Violet 43 | 0.05 | 0.05 | 0.05 | 0.05 |
| Acid Orange 7 | 0.1 | 0.1 | 0.1 | 0.1 |
| γ-Hexanolactone | 10 | 10 | 10 | 10 |
| Ethanol | 2 | 2 | 2 | 2 |
| Lactic acid | 1.8 | 2.7 | 4.5 | 0.77 |
| Caustic soda |  |  | q.s. to pH 3.0 |  |
| Xanthan gum | 1 | 1 | 1 | 1 |

TABLE 2-continued

|  | Invention product, wt. % | | | Comparative product, wt. % |
| --- | --- | --- | --- | --- |
|  | 6 | 7 | 8 | 5 |
| Fragrance | 0.1 | 0.1 | 0.1 | 0.1 |
| Purified water |  |  | Balance |  |
| Buffer capacity (gram eq./L) | 0.006 | 0.012 | 0.031 | 0.003 |
| Dyeing properties for goat's wool | B | A | A | C |
| Shampoo fastness | B | B | A | C |

EXAMPLE 3

Acidic hair dye compositions of the formulations shown in Table 3, respectively, were prepared. In a similar manner as in Example 1(1) (2), their dying properties for goat's wool and their avoidability of staining to the forearm skin were ranked. The results are presented in Table 3.

TABLE 3

|  | Invention product, wt. % | Comparative product, wt. % | |
| --- | --- | --- | --- |
|  | 9 | 6 | 7 |
| Acid Black 1 | 0.4 | 0.4 | 0.4 |
| Benzyl alcohol |  | 5 |  |
| Propylene carbonate |  |  | 20 |
| γ-Hexanolactone | 10 |  |  |
| Ethanol | 2 | 15 | 5 |
| Lactic acid | 5 | 5 | 5 |
| Caustic soda | q.s. to pH 3.0 | q.s. to pH 3.0 | q.s. to pH 4.0 |
| Xanthan gum | 1 | 1 | 2 |
| Fragrance | 0.1 | 0.1 | 0.1 |
| Purified water |  | Balance |  |
| Buffer capacity (gram eq./L) | 0.041 | 0.037 | 0.039 |
| Dyeing properties for goat's wool | A | B | B |
| Shampoo fastness | A | D | B |

Using the fragrance formulations shown in Table 4, hair dye compositions of the formulations shown in Table 5 were prepared, respectively. By a panel of 10 experts, the hair dye compositions were organoleptically ranked for a balance in fragrance and fragrance retention in accordance with the below-described standards. Total scores of the ranking are presented in Table 5.

| Ranking standards | Score |
|---|---|
| Very good | 5 |
| Good | 4 |
| Average | 3 |
| Poor | 2 |
| Bad | 1 |

What is claimed is:

1. A hair dye composition comprising:
   (A) at least one compound selected from the group consisting of γ-hexanolactone, γ-heptanolactone and a mixture thereof and
   (B) an acid dye; and
   having a pH of from 2 to 6 and a buffer capacity not lower than 0.004 gram equivalent/L but lower than 0.2 gram equivalent/L as measured in a form of a tenfold dilute aqueous solution.

2. The hair dye composition according to claim 1, further comprising the following ingredient (C):
   (C) a fragrance composition comprising a combination of a fragrance substance having a ClogP value not greater than 1.5 and another fragrance substance having a ClogP value not smaller than 3.0.

3. The hair dye composition according to claim 1 or 2, further comprising the following ingredient (D):
   (D) at least one organic solvent selected from benzyloxy ethanol, benzyl alcohol, phenoxyethanol,

TABLE 4

| | Fragrance formulation, wt. % | | | |
|---|---|---|---|---|
| Fragrance substance (ClogP) | A | B | C | D |
| Phenylethyl alcohol (1.183) | 10 | 30 | 10 | |
| Phenoxyethyl alcohol (1.188) | 10 | 30 | 10 | |
| Cis-3-hexenol (1.397) | 10 | 10 | | |
| Vanillin (1.354) | 10 | 10 | | |
| Heliotropyl acetate (1.315) | 10 | 10 | | |
| 1-(2,6,6-Trimethyl-2-cyclohexen-1-yl)-2-buten-1-one (3.62) | 10 | | 20 | |
| 5-(2,6,6-Trimethyl-2-cyclohexen-1-yl)-3-methyl-3-buten-2-one (4.019) | 10 | | 20 | |
| 7-Acetyl-1,2,3,4,5,6,7,8-octahydro-1,1,6,7-tetramethyl-naphthalene (4.650) | 10 | 10 | 20 | |
| 3α,6,6,9α-Tetramethyldodecahydronaphtho [2,1-b]furan (5.266) | 10 | | 20 | |
| 4,6,6,7,8,8-Hexamethyl-1,3,4,6,7,8-hexahydrocyclopenta-benzopyran (6.062) | 10 | | | |
| 7-Hydroxy-3,7-dimethyloctan-1-al (1.53) | | | | 20 |
| 3-Phenylpropyl alcohol (1.712) | | | | 20 |
| Benzyl acetone (1.739) | | | | 20 |
| 4-(4-Hydroxy-4-methylpentyl)-3-cyclohexen-1-carboxyaldehyde (2.15) | | | | 20 |
| Methyl (3-oxo-2-pentylcyclopentyl) acetate (2.419) | | | | 20 |
| Total of fragrance ingredients | 100 | 100 | 100 | 100 |

TABLE 5

| | Invention product, wt. % | | | Comparative product, wt. % |
|---|---|---|---|---|
| | 10 | 11 | 12 | 8 |
| Acid Black 1 | 0.1 | 0.1 | 0.1 | 0.1 |
| Acid Violet 43 | 0.05 | 0.05 | 0.05 | 0.05 |
| Acid Orange 7 | 0.1 | 0.1 | 0.1 | 0.1 |
| γ-Hexanolactone | 10 | 10 | 10 | 10 |
| Ethanol | 2 | 2 | 2 | 2 |
| Lactic acid | 4.5 | 4.5 | 4.5 | 4.5 |
| Caustic soda | q.s. to pH 3.0 | q.s. to pH 3.0 | q.s. to pH 3.0 | q.s. to pH 3.0 |
| Xanthan gum | 1 | 1 | 1 | 1 |
| Fragrance | 0.2 (Formulation A) | 0.2 (Formulation B) | 0.2 (Formulation C) | 0.2 (Formulation D) |
| Purified water | Balance | Balance | Balance | Balance |
| Buffer capacity (gram eq./L) | 0.031 | 0.031 | 0.031 | 0.031 |
| Balance in fragrance | 44 | 33 | 35 | 27 |
| Fragrance retention | 41 | 36 | 47 | 19 | phenoxyisopropanol, benzyl glycerol, N-benzyl-formamide, cinnamyl alcohol, phenethyl alcohol, p-anisyl alcohol, ethanol, 1-propanol, 2-propanol, 1-butanol, butoxyethanol, p-methylbenzyl alcohol, methyl carbitol, ethyl carbitol, or propyl carbitol.

4. The hair dye composition according to claim 1 or 2, comprising Acid Orange 7 as said ingredient (B).

5. A method of dyeing hair, which comprises applying onto said hair a hair dye composition according to claim 1 or 2.

6. The hair dye composition of claim 1, wherein, component (A) is present in an amount of 0.5 to 50 wt. %.

7. The hair dye composition of claim 1, wherein, component (B) is present in an amount of 0.05 to 50 wt. %.

8. The hair dye composition of claim 1, wherein, said pH is from 2 to 5.

9. The hair dye composition of claim 1, wherein, said buffer capacity is not lower than 0.01 gram equivalent/L.

10. The hair dye composition of claim 1, wherein, said buffer capacity is not lower than 0.015 gram equivalent/L.

11. The hair dye composition of claim 1, further comprising a water-soluble high-molecular weight substance.

12. The hair dye composition of claim 11, wherein, said a water-soluble high-molecular weight substance is at least one substance selected from the group consisting of gum Arabic, carrageenan, karaya gum, tragacanth gum, carob gum, quience seeds (marmelo), casein, dextrin, gelatin, sodium pectate, sodium alginate, methylcellulose, ethylcellulose, carboxymethyl-cellulose, hydroxyethylcellulose, hydroxypropyl-cellulose, polyvinyl alcohol, poly(vinyl methyl ether), polyvinyl pyrrolidone, sodium polyacrylate, locust bean gum, guar gum, tamarind gum, dialkyldimethylammonium cellulos sulfates, xanthan gum, modified xanthan gum, wellan gum, lavor gum, gellan gum, carboxyvinyl polymer, acrylate ester/methacrylate ester copolymers, a partial crosslinking product of methyl vinyl ehter/maleic anhydride copolymer by 1,9-decadiene, polyethylene glycol, magnesiumaluminumsilicate, bentonite and a mixture thereof.

13. The hair dye composition of claim 11, wherein said a water-soluble high-molecular weight substance is present in an amount of 0.1 to 10 wt. %.

14. The hair dye composition of claim 11, further comprising at least one alcohol selected from the group consisting of a lower alcohol or polyol.

15. The hair dye composition of claim 14, wherein said alcohol is selected from the group consisting of ethanol, 2-propanol, 1-propanol, 1-butanol, ethylene glycol, propylene glycol, isopropylene glycol, 1,3-butylene glycol, glycerine and a mixture thereof.

16. The hair dye composition of claim 14, wherein said alcohol is present in an amount of 0.1 to 30 wt. %.

* * * * *